US008268866B2

(12) United States Patent
Guitton et al.

(10) Patent No.: US 8,268,866 B2
(45) Date of Patent: Sep. 18, 2012

(54) METHODS FOR THE TREATMENT OF TINNITUS INDUCED BY COCHLEAR EXCITOTOXICITY

(76) Inventors: Matthieu Guitton, Le Houlme (FR); Jean-Luc Puel, Cournonterral (FR); Remy Pujol, Montpellier (FR)

( * ) Notice: Subject to any disclaimer, the term of this patent is extended or adjusted under 35 U.S.C. 154(b) by 1512 days.

(21) Appl. No.: 10/812,298

(22) Filed: Mar. 29, 2004

(65) Prior Publication Data

US 2005/0214338 A1    Sep. 29, 2005

(51) Int. Cl.
*A61K 31/4704* (2006.01)
*A61K 31/495* (2006.01)
(52) U.S. Cl. .................................. 514/312; 514/252.12
(58) Field of Classification Search .................. 514/312, 514/650, 252.12
See application file for complete search history.

(56) References Cited

U.S. PATENT DOCUMENTS

| | | | |
|---|---|---|---|
| 3,254,124 A | 5/1966 | Stevens | |
| 5,421,818 A | 6/1995 | Arenberg | |
| 5,474,529 A | 12/1995 | Arenberg | |
| 5,476,446 A | 12/1995 | Arenburg | |
| 5,654,337 A | 8/1997 | Roentsch et al. | |
| 5,716,961 A | 2/1998 | Sands | |
| 5,770,559 A | 6/1998 | Manning et al. | |
| 5,863,927 A | 1/1999 | Smith et al. | |
| 6,017,961 A | 1/2000 | Flores et al. | |
| 6,045,528 A | 4/2000 | Arenberg et al. | |
| 6,066,652 A | 5/2000 | Zenner et al. | |
| 6,120,484 A | 9/2000 | Silverstein | |
| 6,265,379 B1 * | 7/2001 | Donovan | 514/14 |
| 6,309,410 B1 | 10/2001 | Kuzma et al. | |
| 6,316,428 B1 | 11/2001 | Crandall | |
| 6,377,849 B1 | 4/2002 | Lenarz et al. | |
| 6,638,081 B2 | 10/2003 | Korsunsky | |
| 6,656,172 B1 | 12/2003 | Hildebrand | |
| 2002/0068718 A1 | 6/2002 | Pierce | |
| 2002/0082554 A1 | 6/2002 | Lenarz et al. | |
| 2002/0161033 A1 | 10/2002 | Przewosny et al. | |
| 2003/0082214 A1 | 5/2003 | Williams et al. | |
| 2003/0143195 A1 | 7/2003 | Pinsker | |
| 2004/0062819 A1 | 4/2004 | Hildebrand | |
| 2004/0101560 A1 | 5/2004 | Sawchuk et al. | |

FOREIGN PATENT DOCUMENTS

| | | |
|---|---|---|
| CA | 2548892 | 6/2005 |
| DE | 2062620 | 12/1969 |
| DE | 10124953 A1 | 12/2002 |
| JP | 2001187737 | 7/2001 |

(Continued)

OTHER PUBLICATIONS

Tabuchi et al. Effect of ketamine, dextromethorphan, and MK-801 on cochlear dysfunction induced by transient ischemia. Ann. Otol. Rhinol Laryngol 111:2002 p. 44-49.*

(Continued)

*Primary Examiner* — Jennifer M Kim
(74) *Attorney, Agent, or Firm* — Fanelli Haag & Kilger PLLC

(57) ABSTRACT

The invention relates to methods for the prevention and/or treatment of tinnitus induced by cochlear excitotoxicity. In these methods, a pharmaceutical composition comprising an NMDA receptor antagonist is administered to an individual in need of such treatment by appropriate devices and/or formulations for local administration to the inner ear. The tinnitus to be prevented and/or treated may be provoked by acoustic trauma, presbycusis, ischemia, anoxia, sudden deafness, or other cochlear excitotoxic-inducing occurrence.

12 Claims, 5 Drawing Sheets

CAP audiograms after trauma

FOREIGN PATENT DOCUMENTS

| | | |
|---|---|---|
| WO | WO94/08599 | 4/1994 |
| WO | WO 97/38698 | 10/1997 |
| WO | WO98/10757 | 3/1998 |
| WO | WO 98/10757 | 3/1998 |
| WO | WO9810757 | 3/1998 |
| WO | WO01/10833 | 2/2001 |
| WO | WO01/89505 | 11/2001 |
| WO | WO0189505 | 11/2001 |
| WO | WO01/98265 | 12/2001 |
| WO | WO02/15907 A1 | 2/2002 |
| WO | WO02/20481 | 3/2002 |
| WO | WO 03/015699 | 2/2003 |
| WO | WO 2004/022069 | 3/2004 |
| WO | WO2004022069 | 3/2004 |
| WO | WO2004/043902 | 5/2004 |
| WO | WO2004043902 | 5/2004 |
| WO | WO 2004/050021 | 6/2004 |
| WO | WO2004/064912 | 8/2004 |
| WO | WO2004/101072 A1 | 11/2004 |
| WO | WO2005/073237 A | 8/2005 |
| WO | WO2005/094799 | 10/2005 |

OTHER PUBLICATIONS

M.J. Guitton, et al., Cochlear NMDA receptors and tinnitus, Audiological Medicine 2(1): 3-7 (Mar. 2004).
J. Puel et al., Treatment of tinnitus. New perspectives!, Presse Medicale 31(24): 1137-1143 (Jul. 2002).
J.J. Simpson et al., Recent advances in the pharmacological treatment of tinnitus, Trends in Pharmacological Sciences 20(1): 12-18 (Jan. 1999).
M. J. Guitton et al., New pharmacological strategies to restore hearing and treat tinnitus, ACTA OTO-Laryngologica 124(4): 411-15 (May 2004).
J.A. Kaltenbach et al., Plasticity of spontaneous neural activity in the dorsal cochlear nucleus after intense sound exposure, Hearing Res 147 (1-2): 282-292 (Sep. 2000).
M. Kenmochi et al., Salicylate and quinine affect the central nervous system, Hearing Res 113(1-2): 110-116 (1997).
Vesterarger V., Brit. Med. J. 314(7082): 728-731 (1997).
Nicolas-Puel et al., Int. Tinn. J. 8(1): 37-44 (2002).
Olney et al., J. Neuro. Exp. Neurol. 31(3): 464-488 (1972).
Puel, J.L., Prog. Neurobiol. 47(6): 449-76 (1995).
Pujol and Puel, Ann. NY Acad. Sci. 884: 249-254 (1999).
Puel et al., Acta Otolaryngol. 117(2): 214-218 (1997).
Puel et al., Audiol. Neurootol. 7(1): 49-54 (2002).
Puel et al., C.R. Acad. Sci. III. 318(1): 67-75 (1995).
Sattler and Tymianski, Mol. Neurobiol. 24(1-3): 107-129 (2001).
D'Aldin et al., Int. J. Dev. Neurosci. 15(4-5): 619-629 (1997).
Duan et al., Proc. Natl. Acad. Sci. USA 97 (13): 7597-7602 (2000).
Puel et al., J. Comp. Neurol. 341 (2): 241-256 (1994).
Ruel et al., J. Physiol. London 518: 667-680 (1999).
Guitton et al., J. of Neuroscience 23(9): 3944-3952 (2003).
Cazals Y., Prog. Neurobiol. 62: 583-631 (2000).
Vane and Botting, Am. J. Med. 104: 2S-8S (1998).
Miller et al., Nature 355: 722-725 (1992).
Horimoto et al., NeuroReport 7: 2463-2467 (1996).
Casado and Ascher, J. Physiol. 513: 317-330 (1998).
Yamakura and Shimoji, Prog. Neurobiol. 59: 279-298 (1999).
Kemp and McKernan, Nature Neuro. 5, supplement: 1039-1042 (2002).
Chen et al., Audiol. Neurootol. 8: 49-56 (2003).
Vollenweider et al., Eur. Neuropsychopharmacol. 7: 25-38 (1997).
Silverstein et al., Otolaryngology—Head and Neck Surgery 120(5): 649-655 (1999).
Balough et al., Otolaryngology—Head and Neck Surgery 119(5): 427-431 (1998).
Hoffer et al., Otolaryngologic Clinics of North America 36(2): 353-358 (2003).
Wang et al., J. of Neuroscience 23(24): 8596-8607 (2003).
Chen et al., Acta Otolaryngol. Oct. 2003;123(8):905-9.
Denk et al. Otolaryngol (Stockh) 1997; 117(6):825-830.
Domeisen et al. Acta Otolaryngol 1998;118(4):606-608.
Dobie et al., Laryngoscope. Aug. 1999;109(8):1202-11.
Dodson et al., Otolaryngol Clin North Am. Oct. 2004;37(5):991-1000.
Reyes et al., Hear. Res. 171, 43-50, (2002).
Schwab et al., Laryngorhinootologie. Mar. 2004;83(3):164-72.
Ehrenberger Adv Otorhinolaryngol. 2002;59:156-62.
International Preliminary Report on Patentability and International Search Report for PCT/IB2006/003511.
Excerpts of File History of EP05736619, (2009).
Excerpts of File History of U.S. Appl. No. 11/236,941, Oct. 2, 2009.
Willingham, Grand Rounds Archive, Baylor College of Medicine in Houston, Texas, Jul. 22, 2004.
Searchfield et al., Hearing Research 192 (2004) 23-35.
Zhiqiang, Chen et al. "Pharmacokinetics of Caroverine in the Inner Ear and Its Effects on Cochlear Function after Systemic and Local Administrations in Guinea Pigs"; Audiol Neurootol 2003;8:49-56.
Excerpts of File History of EP09005167, Jun. 4, 2009, 11 pgs.
Excerpts of File History of EP05797324, May 27, 2009, 27 pgs.
Boettcher, et al., "Salicylate Ototoxicity: Review and Synthesis". Am J Otolaryngol, 12:33-47, 1991.
Simpson, et al., "Recent advances in the pharmacological treatment of tinnitus", TiPS, vol. 20, pp. 12-18, 1999.
Choi, et al., "Pharmacology of Glutamate Neurotoxicity in Cortical Cell Culture: Attenuation by NMDA Antagonists", The Journal of Neuroscience, 8(1):185-196, 1988.
Japanese Office Action for Japanese Patent Application No. 2007-505480, mailed on Sep. 6, 2011.
English translation of Copy of Japanese Office Action for Japanese Application No. 2007-505480, mailed Sep. 6, 2011, 9 pages.
Notice of Opposition to European patent, Patent No. EP 1 729 753, dated Apr. 22, 2010, 20 pages.
Response to the Opposition Letter of Apr. 22, 2010, EP Patent No. EP1729753, dated Jul 22, 2010, 16 pages.
Decision Rejecting the Opposition of EP Patent No. EP1729753, dated Jan. 13, 2012, 11 pages.
Barrs, et al., "Intratympanic Steroid Injections for Intractable Meniere's Disease" The Laryngoscope, 111(12):2100-2104(2001)("D3").
Parsons, et al., "Memantine is a clinically well tolerated N-methyl-D-asparlale (NMDA) receptor antagonist—a review of preclinical data" Neuropharmacology, 38(6):735-767(1999)("D4").
The English translation of an Office Action mailed from the Japanese Patent Office in JP 2007-505480, pp. 1-10, Sep. 6, 2001.
The English translation of the "Written Argument" mailed from the Japanese Patent Office in JP 2007-50548, pp. 1-12, Sep. 6, 2001.
The English translation of the "Amendment"filed together with the "Written Argument" mailed from the Japanese Patent Office in JP 2007-505480, pp. 1-3, Sep. 6, 2011.
Sahley T. and Nodar R., Hearing Research, 152: 43-54 (2001).
Light J. and Silverstein H., Current Opinion in Otolaryngology & Head and Neck Surgery, 12: 378-383 (2004).
Goycoolea M. and Lundman I., Microscopy Research and Technique, 36:201-211 (1997).
Selivanova et al., Laryngo-Rhino-Otol, 82: 235-239 (2003).
Chandrasekhar S., Otology & Neurotology, 22: 18-23 (2001).
Hoffer et al., Otolaryngologic Clinics of North America, 37:1053-1060 (2004).
Sakata et al., International Tinnitus Journal, 2: 129-135 (1996).
Lenarz et al. 1993, Neural mechanisms of tinnitus. Eur Arch Otorhinolaryngol, vol. 249, pp. 441-446.
Guitton, et al. "m-Chiorophenylpiperazine exacerbates perception of salicylate-induced tinnitus in rats." The European Journal of Neuroscience, vol. 22, No. 10, pp. 2675-2678 (2005).
XP-002401093, Thomson, 2001-605291, JP20000314538, Oct. 16, 2000.
Bespalov, et al., 2000, S-Pb, p. 28. (Russian).
Charkevic, 1980, Medicina, p. 28. (Russian).
Oestreicher, et al., "Different Action of Memantine and Caroverine on Glutamatergic Transmission in the Mammalian Cochlea", Adv. Otohinolaryngol, 2002, pp. 18-25.
Ciocon J. O. et al., "Does oxazepam offer relief of tinnitus or alter it to a non-troublesome functional level in the elderly?" J. of the American Geriatrics Society 45(9):122, Abstract, 1997.

Eggermont Jos. J. et al., "The neuroscience of tinnitus," *Trends in Neurosciences* 27(11): 676-682, 2004.

Mankes David B. et al., "Sodium vaiproate for tinnitus,"*J. of Neurology Neurosurgery and Psychiatry* 65(5): 803, 1998.

Szczepaniak William S, et al., "Effect of L-baciofen and D-baclofen on the auditory system: A study of click-evoked potentials from the inferior colliculus in the rat,"*Annals of Otology Rhinology and Laryngology* 104(5): 399-404, 1995.

Theopold H.M. et al., "[Nimodipine (Bay e 9736) a new therapy concept in diseases of the inner ear?]," *Laryngologie, Rhinologie, Otologie* 64(12): 609-613, 1985.

Vichitrananda C. et al., "Midazolam for the treatment of phantom limb pain exacerbation; preliminary reports," *J. of the Medical Associate of Thailand = Chotmaihet Thangphaet* 84(2): 299-302.

Weber W.E., "[Pharmacotherapy for neuropathic pain caused by injury to the afferent nerve fibers], " *Nederlands Tijdschrift voor Geneeskunde* 145(17): 813-817, Abstract, 2001.

Bauer, C.A. et al., "A behavioral model of chronic Tinnitus in rats,"*Otolaryngol. Head Neck Surg.* 121:457-462, 1999.

Binder, D.K., "The role of BDNF in epilepsy other diseases of the mature nervous system,"*Recent Advances in Epilepsy Research* 34-56, 2004.

Gabellini, N., "Transcriptional reguaItaion by cAMP and $Ca^{++}$ links the $Na^+/Ca^{++}$ exchanger 3 to memory and sensory pathways,"*Mol. Neurbiol.* 30:91-116, 2004.

Guitton, M.J. et al., "Salicylate induces tinnitus through activation of cochlear NMDA receptors,"*J. Nurosci.* 23:3944-3952, 2003.

Ito et al., "A new method for drug application to the inner ear, " *J. Otorhinolaryngol. Relat. Spec.* 272-275, 2005.

Knipper, M. et al., "Thyroid hormone deficiency before the onset of hearing causes irreversible damage to peripheral and central auditory systems," *J. Neurophysiol*83:3101-3112, 2000.

Kumagai, "Effect of intravenous injection of aspirin on the cochlea," *Hokkaido Igaku Tasshi* 67(2):216-233, 1992.

Lang et al., "Association of BNDF serum concentraitions with central sero-tonergic activity; Evidence from auditory signal processing." *Neuropsychopharmacology*30(6):1148-1153, 2005.

Lehner, R. et al., "A new implantable drug delivery system for local therapy of the middle and inner ear," *Ear, Nose Throat* 76:567-570, 1996.

Middleton, C. "The causes and treatments of phantom limb pain. "*Nurs. Times* 99:30-33, 2003.

Schimmang, T. et al., "Lack of BDNF and trkB signaling in the postnatal cochlea leads to a spatial reshaping of innervation along the tonotopic axis and hearing loss, "*Development* 130;4741-4750, 2003.

Stypulkowski, "Mechanisms of salicylate ototoxicity,"*Hear Res*, 46(1-2);113-145.

Timmusk, T. et al., "Identification of brain-derived neurotrophic factor promoter regions mediating tissue-specific, axotomy-, and neuronal activity-induced expression in transgenic mice,"*J. Cell. Biol.* 128:185-199, 1995.

Waddell, A., Canter, R., "Tinnitus, Am. Farm. Physician 69," 591-592, 2004.

Wang et al., "Evaluating effects of some medicine on tinnitus with animal behavioral model rats," *Zhonghua Er. Bi. Yan. Hou. Ke. Za. Zhi.* 35(5): abstract, 2000.

West et al., "Calcium Reguaiation of Neuronal Gene Expression," *Proc. Natl. Acad. Aci. USA* 98;11024-11031, 2001.

Wiechers, B. et al., "A changing pattern of brain-derived neurotrophic factor expression correiates with the rearrangement of fibers during cochlea development of rats and mice," *J. Neurosci.* 19:3033-3042, 1999.

Maier C. et al., "Efficacy of the NMDA-receptor antagonist memantine in patients with chronic phantom limb pain-results of a randomized double-blinded, placebo-controlled trial,"*Pain* 103;277-283, 2003.

Barnea G, et al., Tinnitus with normal hearing sensitivity: extended hight-frequency audiometry and auditory-nerve brain-stem-evoked responses, Audiology. 1990;29(1):36-45.

Chung DY, et al., Factors affecting the prevalence of tinnitus, Audiology. 1984;23(5):441-452.

Coad ML, et al., Characteristics of patients with gaze-evoked tinnitus, Otol Neurotol. Sep. 2001;22(5):650-654.

Diamond C, et al., Systematic review of intratympanic gentamicin in Meniere's disease., J. Otolaryngol. Dec. 2003;32(6):351-361.

Dobie, 2004; Clincal Trials and Drug Therapy for Tinnitus, in: Tinnitus: Theory and Management; BC Decker, Hamilton-London, pp. 266-277.

Ehrenberger K et al., Receptor pharmacological models for inner ear therapies with emphasis on glutamate receptors: a survey, Acta Otolaryngol. Mar. 1995;115(2):236-240.

Frank, 2005, Synthese von dualen NMDA-Rezeptor-/Dopamin-Rezeptor-Liganden, Dissertation, vorgelegt beim FB Biochemie, Chemie and Pharmazie, Johann Wolfgang Geothe-Universitaet Frankfurt am Main.

Hawkins DB et al., Interaural time discrimination ability of listeners with sensorineural hearing loss, Audiology. 1980;19(6):495-507.

House JW et al., Tinnitus: surgical treatment, Ciba Found Symp. 1981;85:204-216.

Koester M et al., [Tinnitus—classification, causes, diagnosis, treatment and prognosis], MMW Fortschr Med. Jan. 15, 2004;146(1-2):23-4, 26-8; quiz 29-30. Review.

Lobarinas E et al., Salicylate- and quinine-induced tinnitus and effects of memantine, Acta Otolaryngol Suppl. Dec. 2006;(556):13-9.

Puel JL et al., Electrophysiological evidence for the presence of NMDA receptors in the guinea pig cochlea, Hear Res. Feb. 1991;51(2):255-64.

Pujol R et al., Implication of non-NMDA and NMDA receptors in cochlear ischemia, Neuroreport. Apr. 1992;3(4):299-302.

Wang J et al., Effects of selective inner hair cell loss on auditory nerve fiber threshold, tuning and spontaneous and driven discharge rate, Hear Res. May 1997;107(1-2):67-82.

Azevdo et al., 2000, Anesth Analg, pp. 1479-1482.

Togal T. et al., 2004, European Journal of Anaesthesiology, pp. 193-197.

Shulman A., International Tinnitus Journal, vol. 3, No. 2, 77-93 (1997).

Alpini D. et al., Tinnitus: pharmacological topodiagnosis, int Tinnitus J. 2004; 10(1):91-3.

Baguley DM., Mechanisms of tinnitus, Br Med Bull, 2002;63:195-212. Review.

Battaglia A et al., Involvement of ras activation on toxic hair cell damage of the marnmallian cochlea, Neuroscience 2003;122(4):1025-35.

Bauer CA et al., Assessing tinitus and prospective tinnitus therapeutics using a psychophysical animal model, J Assoc. Res Cholarymgol. Mar. 2001;2(1);54-64.

Bauer, 2003, Animal models of tinnitus, Otolaryngol Clin N Am, vol 36, pp. 267-285.

Bodmer D et al., Rescue of auditory hair cells from aminoglycoside toxicity by Clostridium difficile toxin B, an inhibitor of the small GTPases Rho/Rac/Cdc42, Hear Res. Oct. 2002;172(1-2):81-6.

Borsello T et al., A peptide inhibitor of c-Jun N-terminal kinase protects against excitotoxicity and cerebal ischemia, Nat Med. Sep. 2003;9(9):1180-6. Epub Aug. 24, 2003.

Cahani M et al., Tinnitus pitch and acoustic trauma, Audiology. 1983;22(4):357-63.

Del Bo L et al., Tinnitus aurium in persons with normal hearing: 55 years later, Otolaryngol Head Neck Surg. Sep. 2008;139(3):391-4.

Dolly JO et al., The structure and mode of action of different botulinum toxins, Eur J Neurol. Dec. 2006;13 Suppl 4:1-9. Review.

Dravid SM et al., Subunit-specific mechanisms and proton sensitivity of NMDA receptor channel block, J Physiol, May 15, 2007;581(Pt 1):107-128. Epub Feb. 15, 2007.

Ehrenberger K., Topical administration of Caroverine in somatic tinnitus treatment: proof-of-concept study. Int Tinnitus J. 2005;11(1):34-7.

Fitzgibbons Pl et al., Gap detection in normal and hearing-impaired listeners, J Acoust Soc Am. Sep. 1982;72(3):761-5.

Lockwood AH et al., The functional anatomy of gazw-evoked tinnitus and sustained lateral gaze, Neurology, Feb. 27, 2001;56(4):472-80.

Niedzielsld AS et al., Expression of AMPA, kainate, and NMDA receptor subunits in cochlear and vestibular ganglia, J Neurosci. Mar. 1995;15(3 Pt 2):2338-53.

Oestreicher E et al., Memantine suppresses the glutamatergic neurotransmission of mammalian inner hair cells, ORL J Otorhinolaryngol Relat Spec, Jan.-Feb. 1998;60(1):18-21.

Pirvola U et al., Rescue of hearing, auditory hair cells, and neurons by CEP-1347/KT7515, an inhibitor of c-Jun N-terminal kinase activation, J Neurosci. Jan. 1, 2000;20(1):43-50.

Ruel J et al., Salicylate enables cochlear arachidonic-acid-sensitive NMDA receptor responces, J Neurosci. Jul. 16, 2008; 28(29); 7313-23.

Sala T., Transtympanic administration of aminoglycosides in patients with Meniére's disease, Arch Otorhinolaryngol. 1988;245(5):293-6.

Scarpidis U et al., Arrest of apoptosis in auditory neurons: Implications for sensorineural preservation in cochlear implantaition, Otol Neurotol, May 2003;24(3):409-17.

Ylikoski J et al., Blockade of c-Jun N-terminal kinase pathway attenuates gentamicin-induced cochlear and vestibular hair cell death, Hear Res. Apr. 2002;166(1-2):33-43.

Zine A et al., The MAPK/JNK signaling pathway offers potential therapeutic targets for the prevention if acquired deafness, Curr Drug Targets CNS Neurol Disord. Aug. 2004:3(4):325-332. Review.

International Pharmaceutical Excipients Council Japan translate edition, "Poloxamer", Handbook of Pharmaceutical Excipients revised edition, Yakuji Nippo Limited, Feb. 28, 2007, pp. 910 through 914.

Pfenninger E, et al, Neuroprotektion durch Ketamin auf zellularer Ebene (Neuroprotective effects of ketamine on a cellular level), Der Artaestesist, 19973, vol. 46, Suppl. 1, pp. S47-S54.

English abstract of Pfenninger E, et al, Neuroprotektion durch Ketamin auf zellularer Ebene (Neuroprotective effects of ketamine on a cellular level), Der Anaestesist, Mar. 1997, vol. 46, Suppl. 1, pp. S47-S54.

Sun,et al., Salicylate increases the gain of the central auditory system, Neuroscience, Mar. 3, 2009; 159(1): 325-334.

* cited by examiner

Score and false positives, D-JNKI-1

Score and false positives, ketamine

METHODS FOR THE TREATMENT OF TINNITUS INDUCED BY COCHLEAR EXCITOTOXICITY

BACKGROUND OF THE INVENTION

1. Field of the Invention

This invention relates to methods for the delivery of pharmaceutical compounds to the inner ear for the treatment of tinnitus induced by cochlear excitotoxicity. Specifically, this invention relates to the local administration of N-Methyl-D-Aspartate (NMDA) receptor antagonists to the inner ear to suppress the NMDA receptor mediated aberrant activity of the auditory nerve following acute, repeated or prolonged or chronic occurrences of cochlear excitotoxicity provoked by incidents such as acoustic trauma, presbycusis, ischemia, anoxia, or sudden deafness and thus, block tinnitus in the case of such incidents.

2. Description of Related Art

Tinnitus, the perception of sound without external acoustic stimulation, is a very common inner ear disorder. It is estimated that 8.6 million Americans, about 3 percent of the U.S. population, suffer from chronic tinnitus (Centers for Disease Control and Prevention, Vital and Health Statistics, Series 10, #200, October 1999). According to the American Speech-Language-Hearing Association (ASHA), a million or more persons find that their tinnitus prevents them from leading a normal life (0.3% of the population). European population studies estimate 7% to 14% of the population have talked with their physician about tinnitus, while potentially disabling tinnitus occurs in approximately 1% to 2.4% of people (Vesterarger V., *British Medical Journal* 314 (7082): 728-731 (1997)).

In spite of the high prevalence of tinnitus and its severe impact on the health and quality of life of people affected by it, there is no truly effective treatment available. Current therapy approaches include the avoidance of ototoxic medications, reduced consumption of alcohol, caffeine and nicotine, reduced stress, the use of background noises or wearable tinnitus maskers (some in combination with hearing aids), behavioral therapies such as hypnosis, cognitive therapy and biofeedback, tinnitus retraining therapy (TRT), pharmacological and other complementary therapies.

Tinnitus is not a disease, but rather a symptom common to various hearing disorders, just as pain accompanies many different illnesses. It is most frequently associated with noise-induced hearing loss, presbycusis and Ménière's Disease (Nicolas-Puel et al., *International Tinnitus Journal* 8 (1): 37-44 (2002)). Other, less frequent origins include exposure to ototoxic drugs (aminoglycoside antibiotics, high-dose loop diuretics, nonsteroidal anti-inflammatory drugs and certain chemotherapeutic agents), reduced vascular flow (ischemia), autoimmune processes, infectious diseases, conductive hearing loss, otosclerosis, head trauma etc. In over 90% of cases, tinnitus is associated with hearing loss of known origin, and well over 70% originate within the inner ear (Nicolas-Puel et al., *International Tinnitus Journal* 8 (1): 37-44 (2002)).

Over the past decade, major advances in the research of the physiopathology of the inner ear resulted in the identification of the key role of the inner hair cell synaptic complex in the development of tinnitus induced by cochlear excitotoxicity, one of the most frequent triggers of tinnitus. Excitotoxicity, which was first described by Olney et al., *J. Neuropathol. Exp. Neurol.* 31(3): 464-488 (1972), is generally characterized as an excessive synaptic release of glutamate, which is the most important neurotransmitter in the Central Nervous System as well as in the auditory system. It activates postsynaptic glutamate receptors (ionotropic and metabotropic), which leads to depolarization and neuronal excitation. However, if receptor activation becomes excessive by an excessive release of glutamate as in the case of excitotoxicity, the target neurones are damaged and may eventually die (Puel J. L, *Prog Neurobiol.* 47(6): 449-76 (1995)).

Cochlear excitotoxicity is provoked either by exposure to excessive noise such as in the case of acute or repeated acoustic trauma (which leads to noise-induced hearing loss or presbycusis), sudden deafness or anoxia/ischemia (Pujol and Puel, *Ann. NY Acad. Sci.* 884: 249-254 (1999)). The release of excessive amounts of glutamate is induced either by excessive sound pressure entering the cochlea in the case of acoustic trauma or by reduced blood flow to the glutamate regulating system in the cases of anoxia/ischemia and sudden deafness. In all cases, excitotoxicity is characterized by a two-step mechanism (Puel et al., *Acta Otolaryngol.* 117 (2): 214-218 (1997)): first, there is an acute swelling of the type I afferent dendrites mediated by the ionotropic glutamate receptors, which leads to a disruption of the postsynaptic structures and a loss of function. Within the next 5 days, synaptic repair (neo-synaptogenesis) is observed with a full or partial recovery of cochlear potentials. The second phase of excitotoxicity, which may develop after strong and/or repetitive injury, consists of a cascade of metabolic events triggered by the entry of $Ca^{2+}$, which leads to neuronal death in the spiral ganglion.

Cochlear excitotoxicity may induce tinnitus during the process of rupturing of the postsynaptic structures and, provided the rupture is not terminal, the following neo-synaptogenesis at the inner hair cell synaptic complex (Puel et al., *Audiol. Neurootol* 7 (1): 49-54 (2002)). A key role in functional recovery after excitotoxicity is played by the NMDA receptors, which are not involved in the activity of auditory nerve fibres under physiological conditions (Puel et al., *Audiol. Neurootol.* 7 (1): 49-54 (2002)), but are up-regulated during the process of neo-synaptogenesis (Puel et al., *C. R. Acad. Sci. III.* 318 (1): 67-75 (1995)), mainly owing to their high calcium ($Ca^{2+}$) permeability (Sattler and Tymianski, *Mol. Neurobiol.* 24 (1-3): 107-129 (2001)). As could be shown in an animal model of cochlear synaptic repair mechanisms, blockage of the NMDA receptors by local administration of the NMDA receptor antagonist D-AP5 delayed the functional recovery and the regrowth of auditory dendrites (Gervais D'Aldin et al., *Int. J. Dev. Neurosci.* 15 (4-5): 619-629 (1997)). It could thus be concluded that glutamate, in addition to its role as a fast excitatory neurotransmitter, has a neurotrophic role via the activation of NMDA receptors.

It has been hypothesized that the up-regulation of mRNA of NMDA receptors induced by cochlear excitotoxicity is responsible for abnormal spontaneous "firing" of the auditory nerve fibres, which may be perceived as tinnitus (Puel J.-L. et al., *Audiol. Neurootol.* 7 (1): 49-54 (2002)). During the process of neo-synaptogenesis afferent dendrites are in a critical state, and may thus be particularly susceptible to excitation by the activation of the NMDA receptors. To avoid any such aberrant excitation, and therefore tinnitus, which may well continue infinitely due to incomplete neo-synaptogenesis, a therapeutic strategy would thus seek to specifically antagonize NMDA receptors. As has been demonstrated, the local administration of NMDA receptor antagonists to the cochlea prevents excitotoxicity induced by acoustic trauma or ischemia (Duan et al., *Proc. Natl. Acad. Sci. USA* 97 (13): 7597-7602 (2000); Puel, *Prog. Neurobiol.* 47 (6): 449-476 (1995); Puel et al., *J. Comp. Neurol.* 341 (2): 241-256 (1994)). While excitotoxicity could also be blocked by application of 2-amino-3-(3-hydroxy-5-methylisoxazol-4-yl)propionate (AMPA) or kainate receptor antagonists, as the acute swelling of afferent dendrites primarily occurs via them (Puel et al., *J. Comp. Neurol.* 341 (2): 241-256 (1994)), such an approach would have a potentially significantly negative impact on the auditory function. As fast excitatory neurotransmission between the inner hair cells and the auditory nerve fibres is predominantly mediated by AMPA preferring receptors (Ruel et al., *J. Physiol. London* 518: 667-680 (1999)), their blocking would suppress not only the undesired excessive stimulation of the auditory nerve, but also the desired, regular excitation and thus provoke hearing loss.

The hypothesized implication of NMDA receptors in the generation of tinnitus has so far only been tested and demonstrated in vivo with a behavioral model of salicylate-induced tinnitus (Guitton et al., *J. of Neuroscience* 23 (9): 3944-3952 (2003); International Publication No. WO 2004/022069). The behavioral model, which had to be developed to measure tinnitus, as tinnitus is not directly observable, was based on the active avoidance paradigm: the animals were conditioned to jump onto a pole whenever hearing a particular sound. Administration of salicylate led to a significant increase in the number of jumps even in the absence of external sound (false positives), indicating the perception of tinnitus. Following delivery of the NMDA antagonists MK-801, 7-CK and gacyclidine to the animals' cochleas via the round window membrane the number of false positives decreased significantly, indicating the suppression of tinnitus.

While these results provided for the first time a confirmation of the hypothesized implication of NMDA receptors in the occurrence of tinnitus, they could clearly not be generalized for all kinds of this inner ear disorder, as salicylate-induced tinnitus is a very peculiar form of tinnitus. Salicylate, the active component of aspirin, has been known for more than a century to induce tinnitus if taken in large doses (Cazals Y., *Prog. Neurobiol.* 62: 583-631 (2000)). It may provoke similar sensations of tinnitus as in the case of cochlear excitotoxicity or other cases with different origin, but it is usually reversible and based on a specific molecular mechanism. Application of mefenamate, a well known cyclooxygenase inhibitor, instead of salicylate also increased the number of false positive responses, suggesting that salicylate-induced tinnitus is related to an inhibition of cyclooxygenase pathway. While tinnitus induced by cochlear excitotoxicity is the result of a cascade of glutamate mediated processes leading to the up-regulation of mRNA of NMDA receptors, salicylate-induced tinnitus is mediated by changes in the arachidonic acid metabolism (see e.g. Cazals Y., *Prog. Neurobiol.* 62: 583-631 (2000)). Salicylate has been shown to inhibit cyclooxygenase activity (see e.g. Vane and Botting, *Am. J. Med.* 104: 2S-8S (1998)). Evidence demonstrates that arachidonic acid potentiates NMDA receptor currents (Miller et al., *Nature* 355: 722-725 (1992); Horimoto et al., *NeuroReport* 7: 2463-2467 (1996); Casado and Ascher, *J. Physiol.* 513: 317-330 (1998)). Electrophysiological studies have demonstrated that arachidonic acid increases the channel opening probability of NMDA receptor in various systems, including cerebellar granule cells, dissociated pyramidal cells, cortical neurons, and adult hippocampal slices (see e.g. Miller et al., *Nature* 355: 722-725 (1992); Horimoto et al., *NeuroReport* 7: 2463-2467 (1996); Yamakura and Shimoji, *Prog. Neurobiol.* 59: 279-298 (1999)). Unlike tinnitus induced by excitotoxicity, there is thus no morphological damage to the inner hair cell synaptic complex, and in particular to the synaptic ending, involved in salicylate-induced tinnitus.

U.S. Pat. No. 5,716,961 to Sands discloses the administration of an NMDA receptor-specific antagonist for the purpose of treating tinnitus. Its neuroprotective properties in the case of glutamate excitotoxicity are demonstrated in cell culture. However, the compound's pharmacological action and efficacy under pathophysiological conditions in vivo are not shown, i.e. there is no relation to tinnitus induced by cochlear excitotoxicity. This must be considered a serious deficiency given the complexities of the inner hair cell synaptic complex. In addition, Sands teaches oral administration of the NMDA receptor antagonist, while discussing topical administration only for cases where a patient is unable to swallow or the oral route of administration is otherwise impaired. Topical administration is discussed nonspecifically in the form of "solutions, lotions, ointments, salves and the like".

Systemic administration of NMDA receptor antagonists to treat inner ear disorders is usually ineffective, as the cochlea is protected like the brain by a biological barrier. Relatively high doses to achieve a desired therapeutic effect would thus be required, but various potent side effects of NMDA receptor antagonists such as reduced learning, memory or motility significantly restrict the maximum tolerable doses. As various studies with humans for the treatment of CNS disorders by NMDA receptor antagonists have shown, plasma levels after systemic administration were consistently below those needed for maximal neuroprotection in animal models, as clinical doses had to be limited due to a number of potentially adverse CNS effects, catatonia, increased blood pressure and anaesthesia (Kemp and McKernan, *Nature Neuroscience* 5, *supplement* 1039-1042 (2002)). On the other hand, it has been shown that local administration of the NMDA-AMPA receptor antagonist caroverine to the inner ear results in higher intracochlear concentrations, while avoiding high secondary concentrations in plasma and cerebrospinal fluid as seen with systemic administration (Chen et al., *Audiol. Neurootol.* 8: 49-56 (2003)).

U.S. Pat. No. 6,066,652 to Zenner et al. discloses a method for treating tinnitus through administration of adamantane, a known NMDA receptor antagonist. The inventors cite results from a clinical study with systemic administration which showed a reduction in tinnitus during treatment. Hypotheses brought forward to explain the results obtained centre on outer hair cells and the presynapse, and do not specifically cover the role of NMDA receptors.

While there are several indications supporting the hypothesis that NMDA receptors play an important role in the genesis of tinnitus induced by cochlear excitotoxicity, the foregoing discussion shows that the molecular mechanisms are still unclear, and that it is therefore not possible to predict reliably whether the use of NMDA receptor antagonists will effectively block this particular type of tinnitus. Further pathophysiological studies on the generation of tinnitus are thus required to validate the hypothesis and develop specific and truly effective therapeutic strategies.

SUMMARY OF THE INVENTION

The invention relates to methods for preventing and/or treating tinnitus induced by cochlear excitotoxicity in a human. The methods include administering to a human a therapeutically effective amount of a pharmaceutical composition comprising an NMDA receptor antagonist. In a method for treating tinnitus, the NMDA receptor antagonist administered is effective to suppress or reduce NMDA receptor mediated aberrant activity of the auditory nerve in the human in need of such treatment. In a method for preventing tinnitus, the NMDA receptor antagonist administered is effective to prevent NMDA receptor mediated aberrant activity of the auditory nerve in the human in need of such treatment. The tinnitus to be prevented and/or treated may be provoked by acoustic trauma, presbycusis, ischemia, anoxia, sudden deafness, or other cochlear excitotoxic-inducing occurrence.

DETAILED DESCRIPTION OF THE INVENTION

Overview

Figure 1:
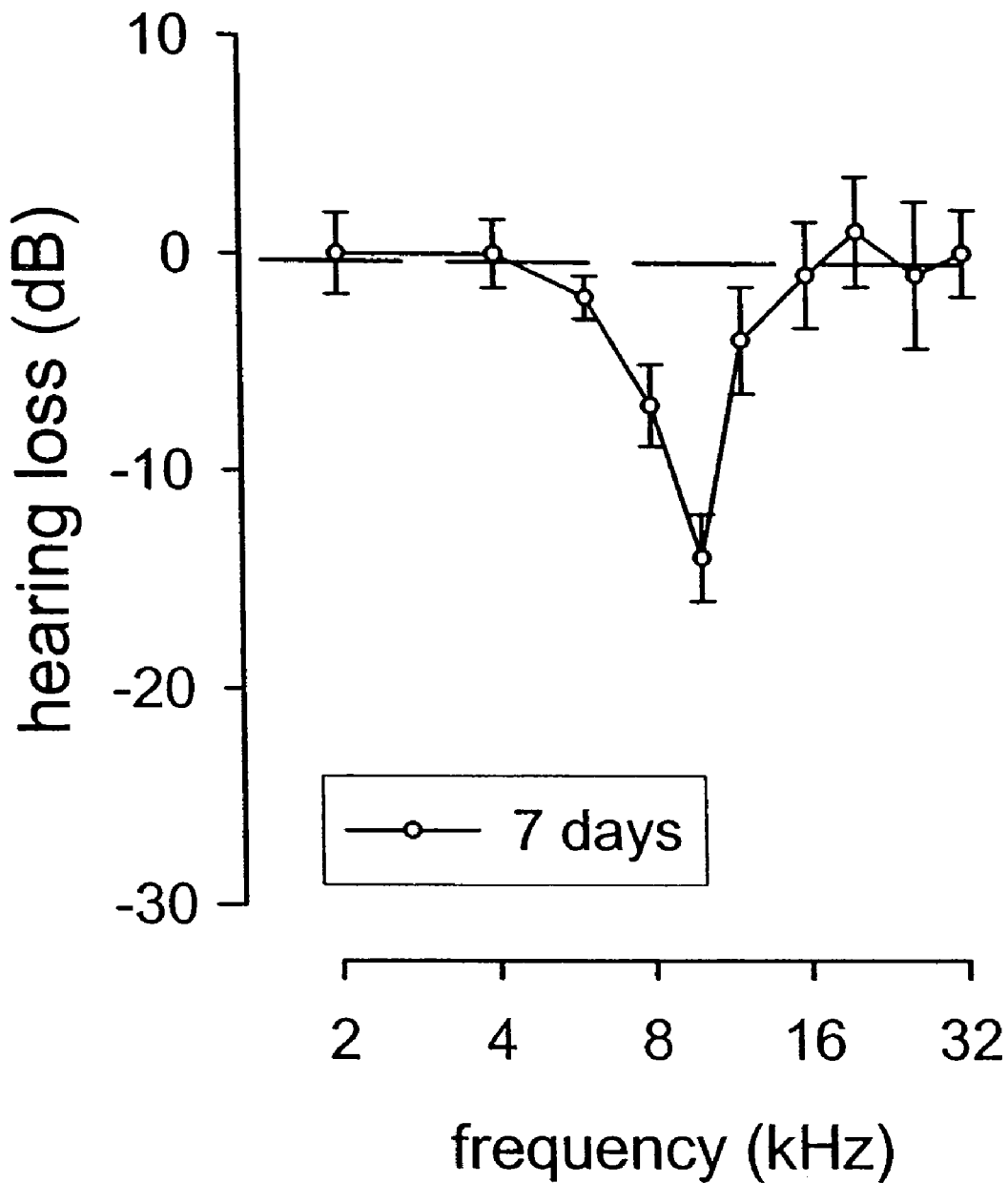
FIG. 1 shows CAP measurements 7 days after trauma in control animals. Hearing loss induced by acoustic trauma was assessed by recording CAP measurements 7 days after trauma. A permanent threshold shift of maximally 13 dB±2.0 was observed at 10 kHz on the seventh day following acoustic trauma.

The present invention is based on experimental findings with an animal model of tinnitus induced by cochlear excitotoxicity. The invention relates to the use of pharmaceutical compounds that act specifically as NMDA receptor antagonists. While not wishing to be bound by theory, it is believed that an NMDA receptor antagonist of the present invention binds to the NMDA receptor at one of its various binding sites, thereby blocking (partly or entirely) the opening of the receptor's ion channel. The NMDA receptor is activated in a complex manner such that both glutamate and glycine binding are required to open the ion channel and permit calcium entry (Kemp and McKernan, *Nature Neuroscience* 5, *supplement:* 1039-1042 (2002)). Glutamate has the neurotransmitter role, as it is released from presynaptic terminals in an activity-dependent manner, whereas glycine acts as a modulator, which is present in the extracellular fluid at more constant levels. The ion-channel integral to the NMDA receptor is voltage-dependently blocked by magnesium, and depolarization removes this block. Binding of an NMDA receptor antagonist to either of the three antagonist sites results in partial or complete blockage of the NMDA receptor and hence blocks or reduces the opening of the ion channel and depolarization of the neuron. The NMDA receptor antagonist thus suppresses the aberrant excitation of the auditory nerve through up-regulated NMDA receptors which may follow cochlear excitotoxicity and thus also reduces or eliminates the perception of tinnitus. Following delivery of the NMDA receptor antagonist, the NMDA receptors are no longer up-regulated. By targeting specifically NMDA receptors, which are only up-regulated under pathophysiological conditions, to suppress the NMDA receptor mediated aberrant activity of the auditory nerve, undesired side-effects on hearing can be avoided, as normal auditory neurotransmission is primarily mediated by AMPA receptors.

In one embodiment, the invention relates to a method for treating tinnitus induced by cochlear excitotoxicity in a human. The method comprises administering to a human a therapeutically effective amount of a pharmaceutical composition comprising an NMDA receptor antagonist. The NMDA receptor antagonist is administered in an amount and for a period of time, effective to suppress or reduce NMDA receptor-mediated aberrant activity of the auditory nerve in a human in need of such treatment. Suppression or reduction of the NMDA receptor-mediated aberrant activity of the auditory nerve results in suppression or reduction of the tinnitus in the treated individual. In a preferred embodiment of this method, the NMDA receptor antagonist is administered after or during the human's exposure to a cochlear excitotoxic-inducing occurrence.

In another embodiment, the invention relates to a method for preventing tinnitus induced by cochlear excitotoxicity in a human. This method comprises administering to a human a therapeutically effective amount of a pharmaceutical composition comprising an NMDA receptor antagonist. In this method the NMDA receptor antagonist is administered in an amount and for a period of time, effective to prevent NMDA receptor-mediated aberrant activity of the auditory nerve in an individual in need of such treatment. Prevention of NMDA receptor-mediated aberrant activity of the auditory nerve prevents tinnitus in the treated individual. In a preferred embodiment of this method, the NMDA receptor antagonist is administered prior to or during the human's exposure to a potential cochlear excitotoxic-inducing occurrence. It is an object of the present invention to prevent and/or treat tinnitus which has been induced by cochlear excitotoxicity. It is not a requirement that the tinnitus induced by cochlear excitotoxicity be provoked by any specific type of occurrence, only that the occurrence provoke cochlear excitotoxicity and induce tinnitus. It is not necessarily a requirement that the nature of the occurrence be known in preventing and/or treating tinnitus. The tinnitus prevented and/or treated may be acute, subacute, or chronic.

It is known in the art that tinnitus results from cochlear excitotoxicity following acoustic trauma, prebycusis, ischemia, anoxia, and/or sudden deafness. The prevention of tinnitus induced by acoustic trauma is exemplified herein. One of skill in the art would predict with a high degree of certainty that the methods provided herein would be effective in preventing and/or treating tinnitus induced not only by acoustic trauma, but also by prebycusis, ischemia, anoxia, and/or sudden deafness since tinnitus resulting from all such occurrences share a common mechanistic cause. The acoustic trauma, prebycusis, ischemia, anoxia, and/or sudden deafness may be characterized as acute, repeated, or prolonged. One of skill in the art would predict that the methods of the present invention would be effective in preventing and/or treating tinnitus induced by means other than acoustic trauma, prebycusis, ischemia, anoxia, and/or sudden deafness as long as the tinnitus is induced by cochlear excitotoxicity. The cochlear excitoxicity resulting from such occurrences may be characterized as acute, repeated, or prolonged, depending on the duration of the cochlear excitotoxic-inducing occurrence.

Compound

Formulations of the pharmaceutical compounds to be administered in connection with the methods of the present invention comprise a selective NMDA receptor antagonist which binds to the NMDA receptor either at the competitive NMDA antagonist binding site, the non-competitive NMDA antagonist binding site within the ion channel, or to the glycine site. Exemplary compounds include, but are not necessarily limited to, ifenprodil, Ketamine, memantine, dizocilpine (MK-801), gacyclidine, traxoprodil (non-competitive NMDA antagonists), D-2-amino-5-phosphonopentanoic acid (D-AP5), 3-((±)2-carboxypiperazin-4-yl)-propyl-1-phosphonic acid (CPP; both competitive NMDA antagonists), 7-chlorokynurenate (7-CK), Licostinel (glycine site antagonists). An NMDA antagonist for use in the present invention may be any derivative, analogue, and/or enantiomeric form of an NMDA antagonist thereof which retains the function of an NMDA antagonist. Among NMDA antagonists, Ketamine is considered one of the preferred compounds. Ketamine ($C_{13}H_{16}ClNO$, 2-(2-chlorophenyl)-2-(methylamino)-cyclohexanone) is a non-competitive NMDA-receptor antagonist which binds to the PCP-binding site, a separate site of the NMDA-receptor complex located within the ion channel, thereby blocking the transmembranous ion flux. More specifically, the preferred compound is (S)-Ketamine, as it binds with a 3-4-fold higher affinity to the PCP binding site of the NMDA receptor than (R)-ketamine (Vollenweider et al., *Eur. Neuropsychopharmacol.* 7: 25-38 (1997)). The composition for administration in the methods of the present invention may comprise one or more NMDA receptor antagonists.

Administration and Formulation

Delivery of the compound to patients can be accomplished orally, intravenously, subcutaneously, intraperitoneally, intramuscularly, rectally or topically/locally, whereas topical/local administration to the inner ear is generally preferred, as therapeutically effective doses with systemic administration may induce undesired side-effects. One of skill in the art will recognize that administration of an NMDA antagonist in the present invention may be accomplished in a variety of other ways. The only requirement for administration in the present invention is that a therapeutically effective amount of a pharmaceutical composition comprising an NMDA antagonist be able to reach the site of the NMDA receptor mediated aberrant activity of the auditory nerve in the afflicted individual.

Administration of the compound to the inner ear may be accomplished by various delivery techniques. These include the use of devices or drug carriers to transport and/or deliver the compound in a targeted fashion to the membranes of the round or oval window, where it diffuses non-invasively into the inner ear or is actively infused. Non-limiting examples include otowicks (see e.g. U.S. Pat. No. 6,120,484 to Silverstein), round window catheters (see e.g. U.S. Pat. Nos. 5,421,818; 5,474,529; 5,476,446; 6,045,528; all to Arenberg, or U.S. Pat. No. 6,377,849 and its division 2002/0082554 to Lenarz), or various types of gels, foams, fibrins or other drug carriers, which are placed in the round window niche or on the oval window, and loaded with the compound for sustained release (see e.g. WO 97/38698 by Manning; Silverstein et al., *Otolaryngology—Head and Neck Surgery* 120 (5): 649-655 (1999); Balough et al., *Otolaryngology—Head and Neck Surgery* 119 (5): 427-431 (1998)). Delivery techniques further include the use of devices which are inserted invasively into the cochlear duct or any other part of the cochlea (see e.g. U.S. Pat. No. 6,309,410 to Kuzma). The compound may also be administered to the inner ear by transtympanic injection, where the middle ear or part of it is filled by a solution or other carriers of the compound, from where it diffuses non-invasively across the membrane of the round window into the cochlea (see e.g. Hoffer et al., *Otolaryngologic Clinics of North America* 36 (2): 353-358 (2003)). The preferred method of administration to the inner ear is by the non-invasive method of diffusion across the round window membrane, which is relatively easily accessible from the middle ear space, and allows the inner ear to remain intact, thus avoiding any potential problems from leaking intracochlear fluids.

A compound contained within the pharmaceutical composition of this invention may be provided in the form of a pharmaceutically acceptable salt. Examples of such a salt include, but are not limited to, those formed with organic acids (e.g. acetic, lactic, citric, malic, formaric, tartaric, stearic, ascorbic, succinic, benzoic, methanesulfonic, toluenesulfonic, or pamoic acid), inorganic acids (e.g., hydrochloridic, nitric, diphosphoric, sulphuric, or phosphoric acid), and polymeric acids (e.g., tannic acid, carboxymethyl cellulose, polylactic, polyglycolic, or co-polymers of polylactic-glycolic acids).

Pharmaceutical compositions of this invention contain a therapeutically effective amount of active ingredient, and, as may be necessary, inorganic or organic, solid or liquid pharmaceutically acceptable carriers. Pharmaceutical compositions suited for topical/local administration to the inner ear include aqueous solutions or suspensions, which may either be ready to use or require preparation prior to use (e.g. lyophilisates). These formulations may contain viscosity-increasing agents like cellulose derivatives or sucrose acetate isobutyrate. Suited pharmaceutical compositions further include gels, which may be biodegradable or non-biodegradable, aqueous or non-aqueous, or microsphere based. Examples of such a gel include, but are not limited to, carbomers, poloxamers, alginates, hyaluronates, xyloglucans, polyesters, polysaccharides, poly(lactides), poly(glycolide) or their co-polymers PLGA, sucrose acetate isobutyrate, and glycerol monooleate, whereas the gel may be formed in situ or prior to use from solutions or suspensions. They further include creams and ointments, emulsions, micro-emulsions or self-emulsifying compositions. Pharmaceutical compositions suited for enteral or parenteral administration include tablets or gelatine capsules or aqueous solutions or suspensions as described above.

The pharmaceutical compositions may be sterilized and/or may contain adjuvants, e.g. preservatives, stabilizers, wetting agents and/or emulsifiers, salts for regulating the osmotic pressure and/or buffers, penetration enhancers, bio-adhesive agents. The pharmaceutical compositions of the invention may, if desired, contain further pharmacologically active substances, such as, but not limited to antibiotics or analgesics. They may be prepared by any of the methods well known in the art of pharmacy, e.g. by conventional mixing, granulating, confectioning, dissolving or lyophilizing methods, and contain from about 0.01 to 100%, preferably from about 0.1 to 50% (lyophilisates up to 100%), of active ingredient.

The compound can be administered prior to, during or after tinnitus has been induced by excitotoxicity. The amount to be administered may vary, depending upon the method of administration, duration of therapy, the condition of the subject to be treated, the severity of tinnitus and ultimately will be decided by the attending physician. The duration of therapy may range between about one hour and several days, weeks or months, and may extend up to chronic treatment. The therapeutically effective amount of the compound to be delivered may range between about 0.1 nanogram/hour to about 100 micrograms/hour.

A therapeutically effective dose is defined as an amount effective to suppress or reduce NMDA receptor-mediated aberrant activity of the auditory nerve in a treated individual. A therapeutically effective dose is also the amount effective to suppress or reduce tinnitus in the afflicted individual. As stated above, a therapeutically effective dose may vary, depending on the choice of specific NMDA antagonist for treatment and on the method of its administration. For example, a higher dose of an intravenously administered NMDA antagonist would be required than that of the same pharmaceutical composition administered locally to the round window membrane or oval window of the ear. Additionally, a lower dose of an NMDA antagonist would be required wherein the NMDA antagonist of the present invention binds the NMDA receptor with a higher binding affinity than an NMDA antagonist that binds with a lower affinity. As a result, NMDA antagonists with higher binding affinities for the NMDA receptor are preferred. As stated above, (S)-Ketamine, which binds with a 3-4-fold higher affinity to the PCP binding site of the NMDA receptor than (R)-ketamine (Vollenweider et al., *Eur. Neuropsychopharmacol.* 7: 25-38 (1997)) is a preferred compound for use in the methods of the present invention. The duration of therapy may also vary, depending on the specific form of tinnitus for which treatment is desired—acute, subacute, or chronic. As a guide, shorter durations of therapy are preferred and are sufficient when the tinnitus does not recur once therapy has ceased. Longer durations of therapy may be employed for an individual in which tinnitus persists following short therapy.

EXEMPLIFICATION

Example 1

Methods and Materials

We developed and tested an animal model of tinnitus induced by cochlear excitotoxicity, which was provoked by acoustic trauma. As tinnitus in general is not directly observable, as cochlear excitotoxicity does not result in tinnitus in all individuals, and as perceptions of tinnitus may just disappear a few hours after the excitotoxic incident or last forever, the definition and implementation of such an animal model represented a substantial challenge. These considerations mean for example that more animals are required to obtain a sufficient number of tinnitus cases for study and to permit observation of tinnitus over time. As it is unclear whether a case of tinnitus induced by cochlear excitotoxicity is to last or not, it is advisable to conduct studies in its early stages.

The experiments were performed in two stages. First, the hearing loss following acute acoustic trauma as well as the incidence of tinnitus were evaluated with no therapeutic compound administered. In the second stage, the efficacy of three pharmaceutical compounds in suppressing tinnitus was tested: S-(+)-Ketamine, a NMDA receptor antagonist (Sigma-Aldrich), 7-chlorokynurenate (7-CK; Sigma-Aldrich), another NMDA receptor antagonist, which was previously tested in a model of salicylate induced tinnitus (Guitton et al., *J. of Neuroscience* 23 (9): 3944-3952 (2003); International Publication No. WO 2004/022069) as a reference, and D-JNKI-1, a peptide inhibitor of c-Jun N-Terminal kinase (Xigen S. A.), which was shown to protect against auditory hair cell death and hearing loss due to acoustic trauma (Wang et al., *J. of Neuroscience* 23 (24): 8596-8607 (2003)). Experimental results from the first stage (i.e. no pharmaceutical compound used) served as a control.

Animals

Experiments were performed with Long-Evans rats for their superior locomotor capacities compared to other rats. During experiments, animals were caged individually at a constant temperature with a day/night cycle of 12/12 hours. All behavioral tests were performed in the dark phase, the usual period of animal activity, for every animal individually at about the same time each day. Outside the experiments, the animals received water and nutrition ad libitum. A total of 60 animals were used: 30 for the first stage (of which 25 were tested by behavioral techniques and 5 by electrophysiology), and 30 for the second stage with 10 for each pharmaceutical compound tested.

Acute Acoustic Trauma

Acoustic trauma was induced by a continuous pure tone of 6 kHz generated by a waveform synthesizer (Hewlett-Packard 8904A). The animals were anesthetized and exposed to 130 dB sound pressure level (SPL) for 20 minutes, which was routed through a programmable attenuator and presented to the ears in free field via a JBL 075 earphone positioned 10 cm in front of the animal's head. Sound level was measured using a calibrated Bruel and Kjaer microphone (4314) and a Bruel and Kjaer calibrating amplifier (2606).

Behavioral Conditioning and Testing

Animals were conditioned to achieve active avoidance (Guitton et al., *J. of Neuroscience* 23 (9): 3944-3952 (2003); International Publication No. WO 2004/022069). Behavioral testing consisted of the performance of a task whenever a sound was produced in a conditioning box with an electrical floor and a climbing pole. Animal conditioning was achieved in a total of 10 sessions, each lasting between 15 and 20 minutes, with a conditioning stimulus of a pure tone at 50 dB SPL of 3 seconds duration at a frequency of 10 kHz. The unconditional stimulus consisted of an electric shock to the feet of the animals (3.7 mA) during maximally 30 seconds. Interstimulus intervals were 1 second. The electric shocks were stopped by the investigator once the animal correctly climbed onto the pole. Intervals between trials were at least one minute long.

The score was defined as the animal's performance, measured by the number of cases when it climbed correctly onto the pole in response to the sound. As soon as an animal had reached a score of at least 80% in three consecutive sessions, it was considered successfully conditioned and employed in the experiments.

Experiments were conducted daily with measurements of both score and false positive responses during one session of 10 minutes with 10 trials in total. False positive responses were climbings onto the pole between trials without any acoustic stimulation, i.e. during periods of silence. They can be interpreted as the perception of tinnitus, as the animals are performing the task of climbing onto the pole as if they were hearing the stimulus (Guitton et al., *J. of Neuroscience* 23 (9): 3944-3952 (2003); International Publication No. WO 2004/ 022069). Sound stimuli were randomized, and electrical footshocks were only delivered if the animals didn't climb onto the pole in response to sound.

Electrophysiology

The compound action potential (CAP) of the auditory nerve was measured by an electrode implanted onto the round window membrane of the animals (with a reference electrode placed in a neck muscle). The reference electrode and the round window electrode were soldered to a plug fixed on the skull. 10 tone bursts per second (with a duration of 9 ms and a rise/fall cycle of 1 ms) generated by an arbitrary function generator (LeCroy Corp., model 9100R), were applied to the animal's ear in free filed via a JBL 075 earphone. 10 frequencies were tested (2, 4, 6, 8, 10, 12, 16, 20, 26, and 32 kHz) with burst levels from 0 to 100 dB SPL in steps of 5 dB. Auditory nerve responses were amplified (Grass P511K, Astro-Med Inc.), filtered (100 Hz to 3 kHz) and averaged on a PC (Dimension Pentium, Dell). CAP amplitudes were measured peak-to-peak between the first negative depression N1 and the subsequent positive wave P1. The CAP threshold was defined as the sound intensity (in dB SPL) needed to elicit a measurable response (greater than 5 µV).

Pharmacology

Animals were anaesthetized with a single-dose i.p. injection of 0.3 ml/kg of pentobarbital at 6% (Sanofi) and operated under aseptic conditions right after the first behavioral testing (day 0). The two bullae were opened through a posterior auricular surgical procedure (dorsal approach). After exposure of the two cochleas, gelfoam (Gelita tampon, B. Braun Medical AG) impregnated with 2.5 µl artificial perilymph containing the pharmaceutical compounds was placed on the each of the round windows of the two cochleas. The concentration of all three pharmaceutical compounds used was 50 µM. The bullae were then closed with dental cement (Unifast Trad, GC Corporation), the wounds disinfected and sutured. The animals were then exposed to the traumatizing sound. Behavioral tests were resumed 24 hours after the acoustic trauma (day 1), and repeated daily for a total of 8 days.

Statistics

In each behavioral experiment, comparisons of the relevant parameters were made according to a two-way (group×time, with repeated measures on the last factor) analysis of variance (ANOVA) in order to test the measurement effect (group effect), the time effect and the group×time interactions. The ANOVA was followed by post hoc comparisons (Tukey test). Statistical analysis of CAP measurements were made according to a one-way ANOVA followed by Dunnett test. All results were presented as mean±SEM.

Results

Stage 1, No Therapeutic Compound Administered

As expected, the traumatizing sound led to a permanent hearing loss (5 animals tested with electrophysiology). As shown in FIG. 1, a permanent threshold shift of maximally 13 dB±2.0 could be observed at 10 kHz on the $7^{th}$ day after the acoustic trauma (which had occurred on day 1).

Figure 2:
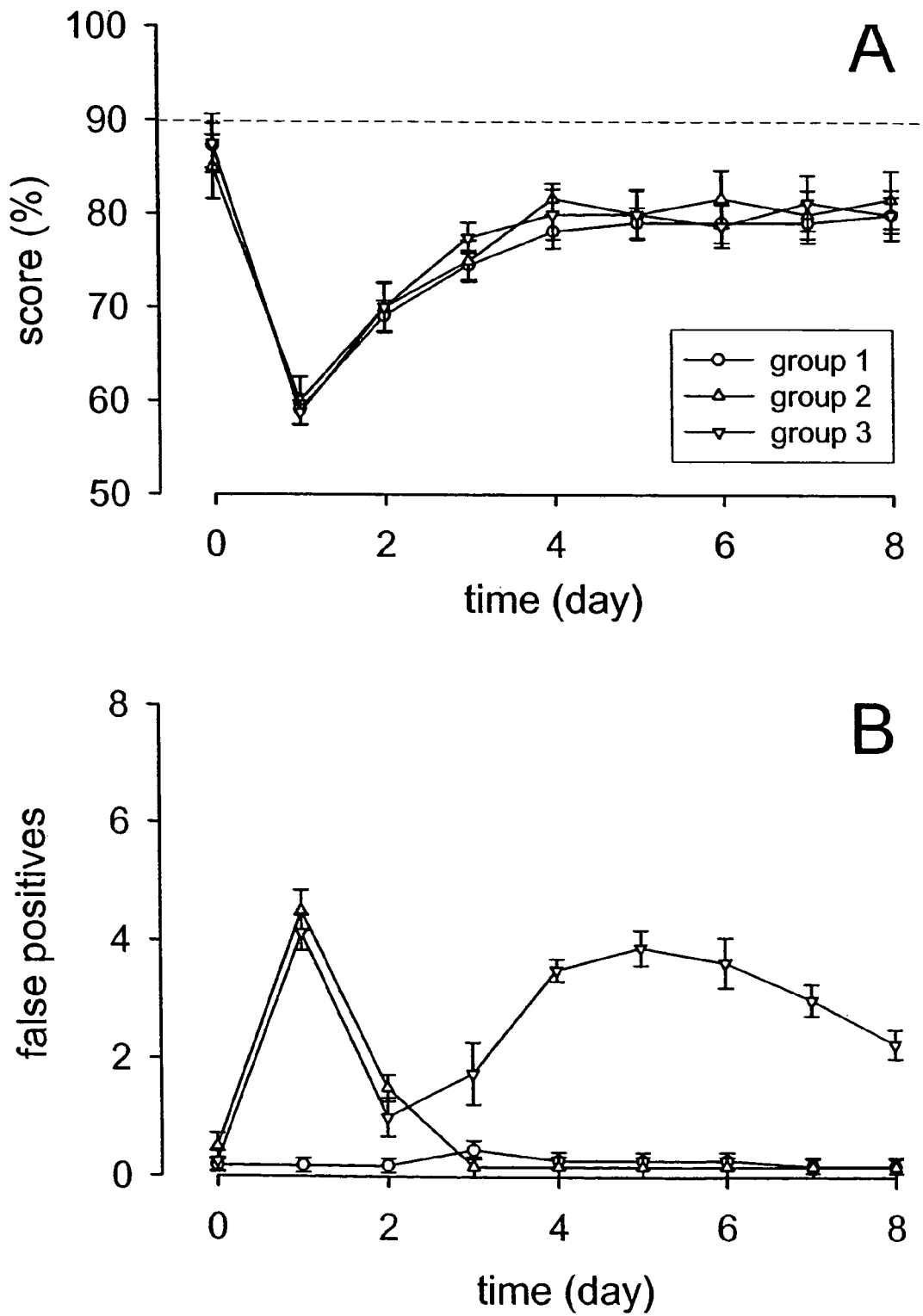
FIG. 2 illustrates the measurement of score and false positive responses following acoustic trauma in control animals. (A) Acoustic trauma led to a decrease in correct behavioral responses to sound stimulation, followed by partial recovery over time, reflecting the induced hearing loss. (B) The number of false positives differed substantially among tested animals following acoustic trauma. Group 1 animals did not experience tinnitus, group 2 animals experienced tinnitus only transiently, while group 3 animals experienced tinnitus both transiently and then permanently.

The acoustic trauma also led to a decrease in score (25 animals tested in the behavioral model). As shown in FIG. 2A, the average score dropped significantly from the high initial level of day 0 (i.e. before the acoustic trauma) of 87%±1.6 to a low of 59%±1.0 on day 1, where the acoustic trauma was provoked ($p<0.001$). Partial functional recovery could be observed from day 2 (69%±1.2), leveling off on day 4 at an average score of 80%±2.0. Statistical analysis of the results showed that the observed decreases in score were significant ($p<0.05$), also from day 2 to day 8 (80%±1.4 on the last day). The reduced ability of animals to react correctly to the conditioned sound stimulus is consistent with the fact that the hearing loss provoked by the traumatizing sound has significantly reduced their ability to hear sound at the frequency of the acoustic stimulus.

Interestingly, it was also found that the number of false positives differed substantially among the animals tested after the acoustic trauma, as shown in FIG. 2B. One group of animals (designated as group 1; n=11) displayed no increase in the number of false positives at all—even after the acoustic trauma (0.18 false positives±0.12 on days 0 and 1). The remaining 14 animals however delivered a significant increase of false positives from 0.34±0.13 on day 0 to 4.28±0.22 on day 1. This rise turned out to be reversible for 6 of them (group 2), with the number of false positives dropping to normal levels again on day 2 and thereafter. The other 8 animals however (group 3) delivered after the transitory increase yet another rise in false positives. The maximum of false positives in this second phase was observed on day 5 with 3.87±0.29, and the effect remained statistically significant through day 8 (2.25±0.25 false positives on that last day of observation). In other words: there was first a reversible increase, which was then followed by a permanent increase in the number of false positive responses to the sound stimulus. This means that after acoustic trauma some animals were experiencing no tinnitus at all (group 1), some only in a transitory form (group 2), and some first in a transitory form and then permanently again for the rest of the observation period. This outcome corresponds in principle to general observations in humans.

Stage 2, Application of Therapeutic Compounds

Figure 3:
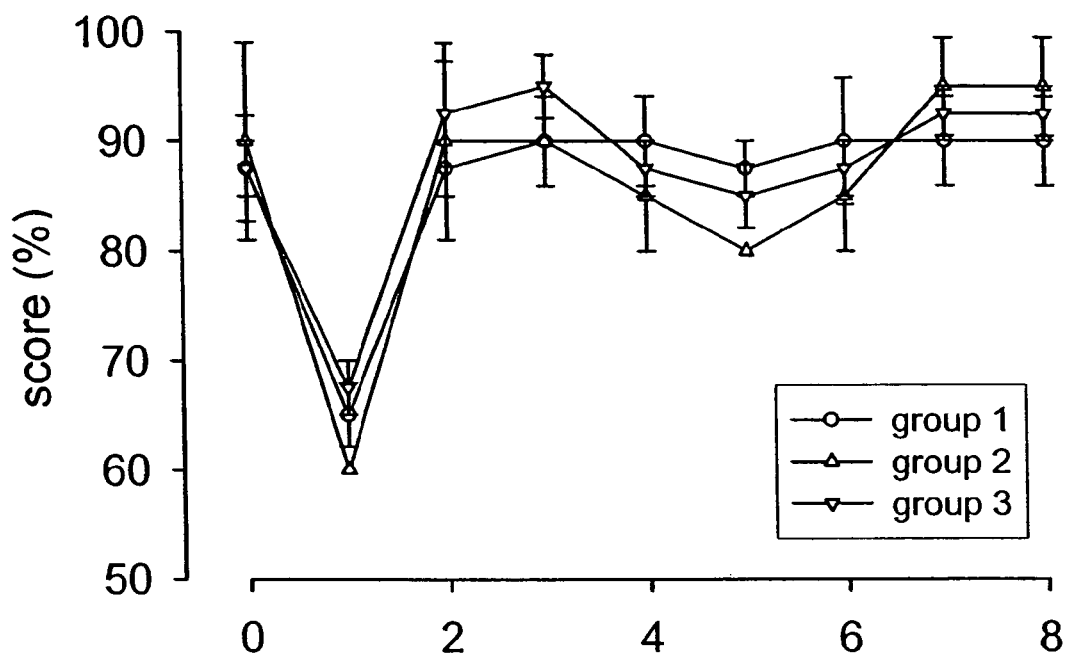
FIG. 3 illustrates that hair cell loss and thus hearing loss induced by acoustic trauma does not play a significant role in the generation of tinnitus. Treatment with D-JNKI-1 prevented hearing loss after acute acoustic trauma, as shown by the rapid recovery of score following trauma (A) but had no significant effect on the prevention of tinnitus, as the prevalence and patterns of tinnitus were essentially the same as in untreated animals (B).
Figure 3:
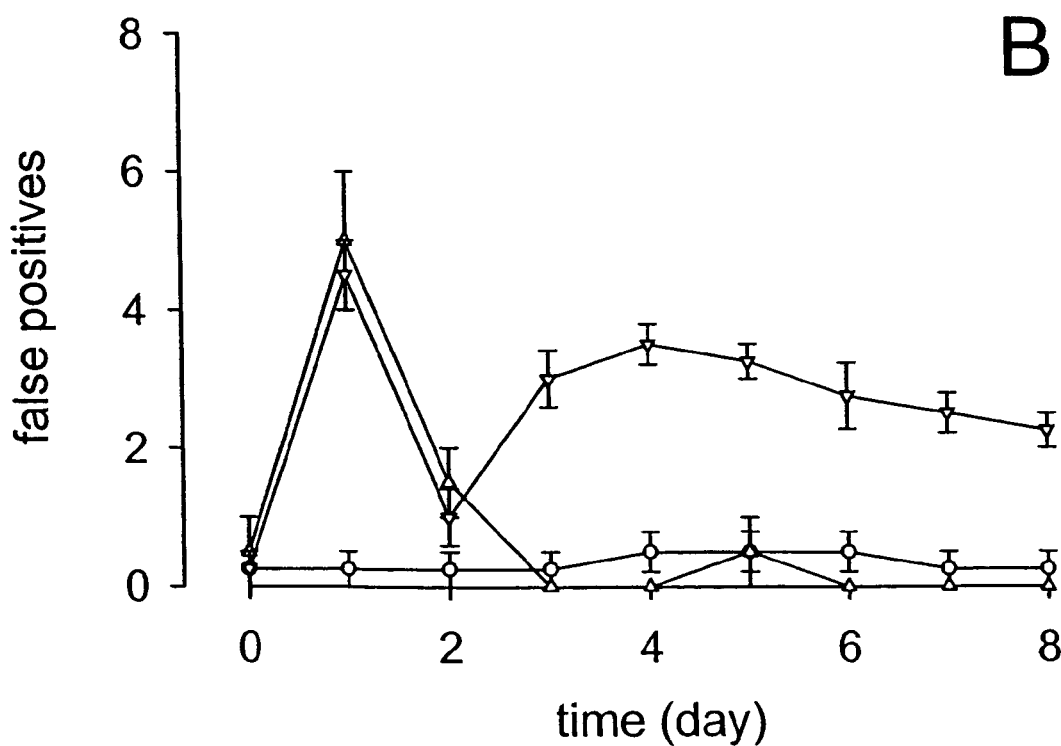

In order to test whether the mechanism underlying the generation of tinnitus by acoustic trauma was linked to the loss of cochlear hair cells and/or to the induction of excitotoxicity, D-JNKI-1 was applied locally to the round window membrane. As shown in FIG. 3A, the pharmaceutical compound could not prevent the decrease of score from day 0 (88%±2.5) to day 1 (65%±1.7). However, treatment resulted in rapid, full functional recovery to pre-traumatic levels on day 2 (90%±2.6), which persisted subsequently (92%±2.0 on day 8).

While D-JNKI-1 prevented permanent hearing loss after acute acoustic trauma, it had no significant effect on the number of false positives and thus the prevention of tinnitus. As FIG. 3B shows, the patterns of false positives are almost identical to the ones observed with the control group (FIG. 2B): while group 1 (n=4) showed no increase at all (0.25±0.25 false positives on both days), the two other groups showed again a statistically significant increase ($p<0.05$) in the number of false positives from day 0 (0.33±0.21) to day 1 (4.66±0.42). As for group 2 (n=2), the increase was again a short-term, fully reversible increase, while the transitory increase in group 3 (n=4) was again followed by a permanent rise in the number of false positives (3.50±0.29 false positives on day 4 and 2.25±0.25 on day 8). Overall, these results suggest that hair cell loss induced by acoustic trauma does not play a significant role in the generation of tinnitus, and point to cochlear excitotoxicity as the mechanism at its base.

Figure 4:
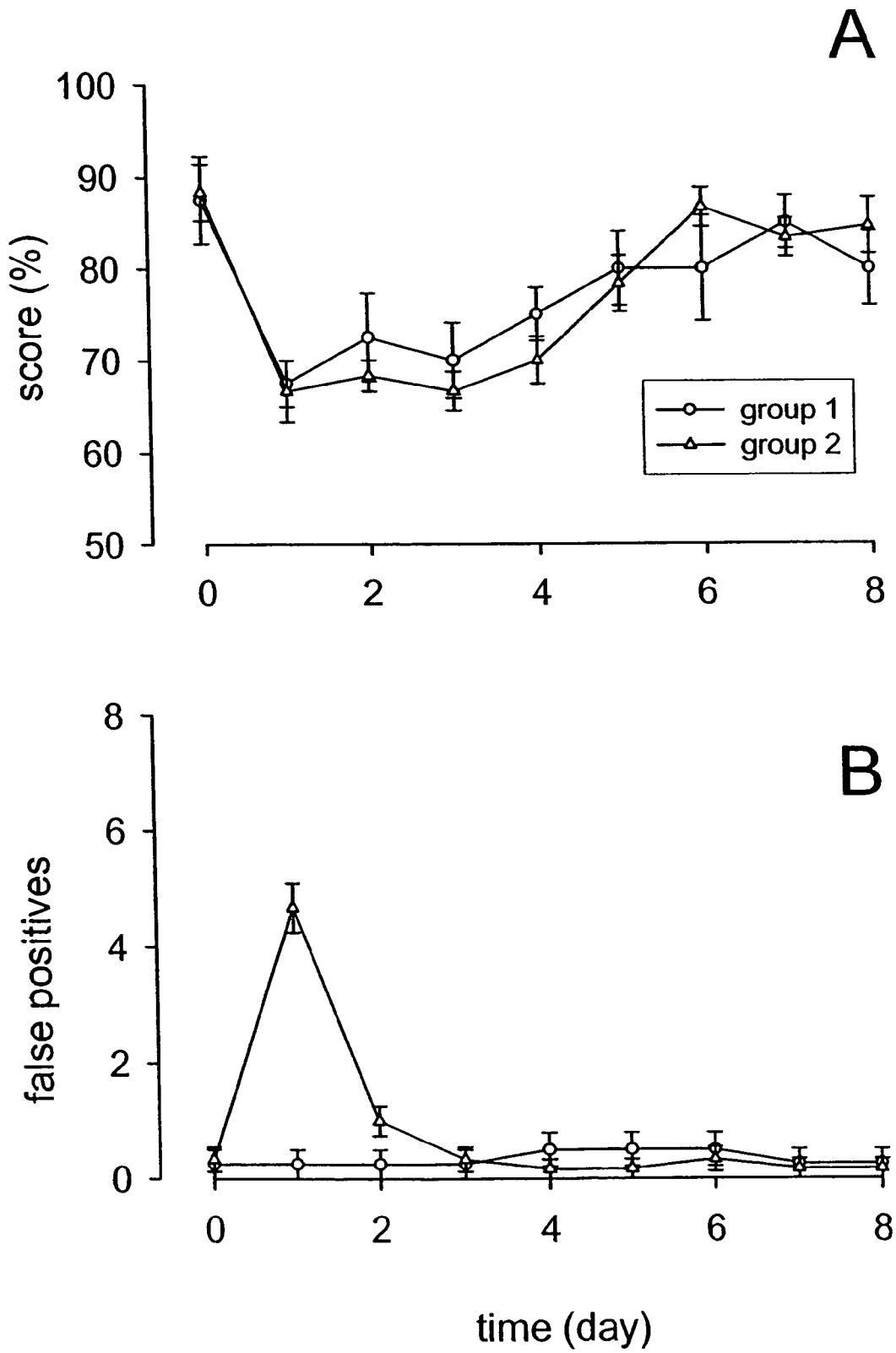
FIG. 4. illustrates that local administration of the NMDA antagonist 7-CK to the round window membrane resulted in the prevention of tinnitus. (A) The average behavioral score dropped from day 0 to day 1 and recovered subsequently; however improvement was slower than in untreated animals. (B) Local administration of the NMDA antagonist 7-CK resulted in suppressing persistent tinnitus induced by cochlear excitotoxicity; only cases of transient tinnitus could be observed.
Figure 5:
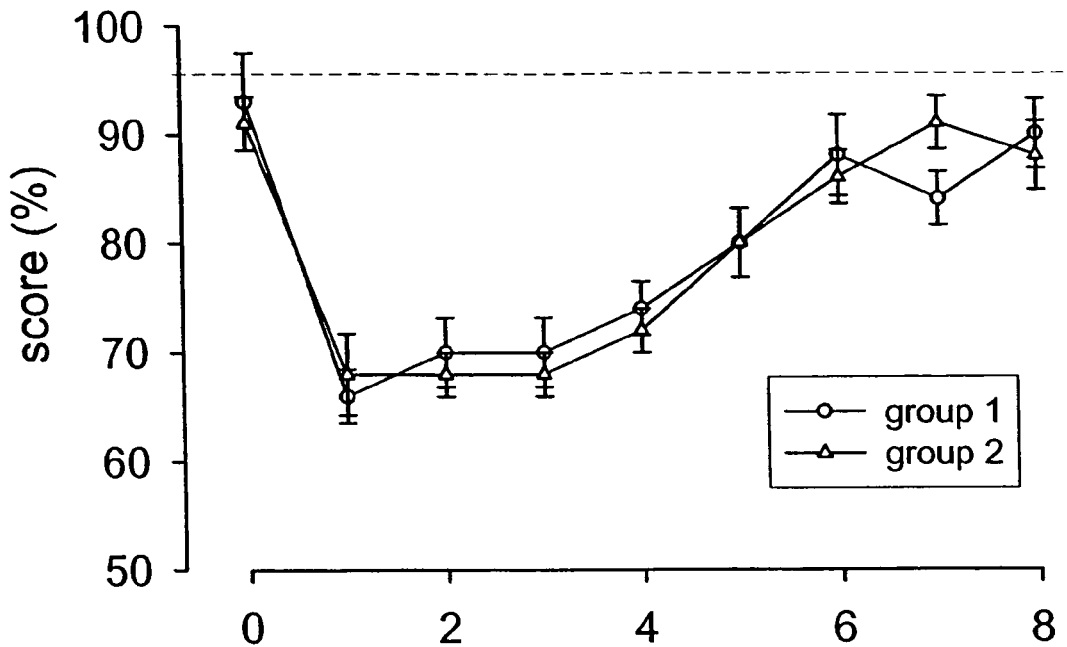
FIG. 5 shows that local administration of the NMDA antagonist S-(+)-Ketamine to the round window membrane resulted in the prevention of persistent tinnitus. (A) The average behavioral score dropped from day 0 to day 1 and recovered subsequently; however improvement was slower than in untreated animals. (B) Local administration of the NMDA antagonist S-(+)-Ketamine resulted in suppressing persistent tinnitus induced by cochlear excitotoxicity since only cases of transient tinnitus could be observed.
Figure 5:
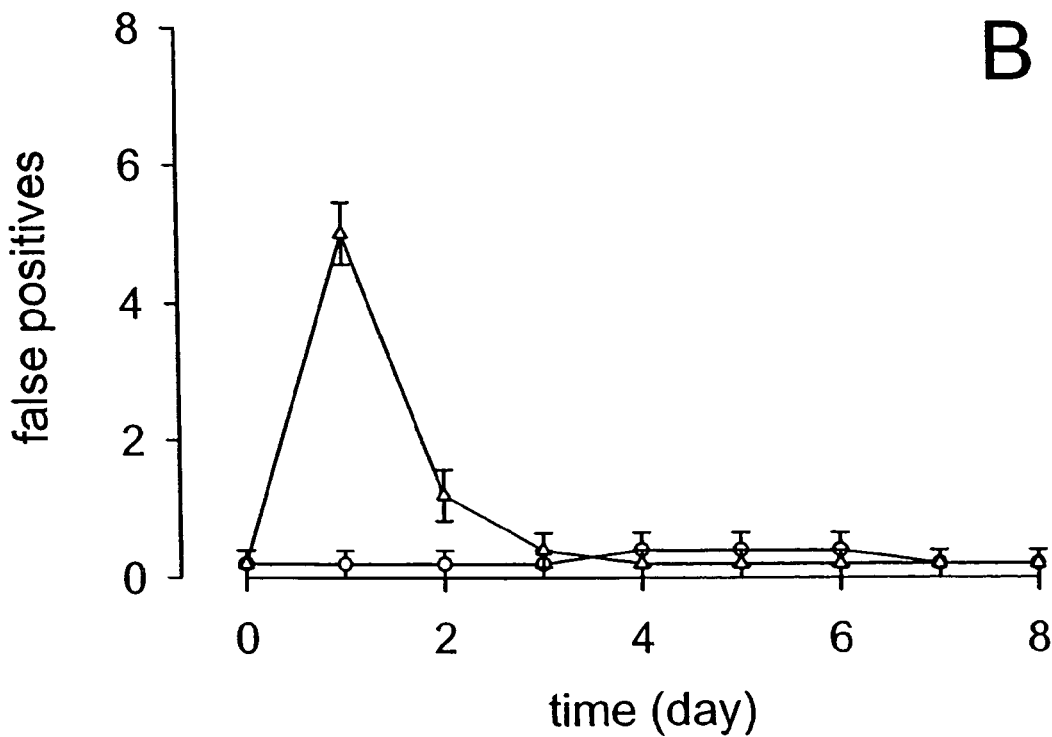

Local application of the two NMDA receptor antagonists 7-CK and S-(+)-Ketamine yielded results, which were very similar to each other. As shown in FIGS. 4A and 5A, the average score dropped significantly from day 0 to day 1 and then recovered, however at a slower rate than in untreated animals. In contrast to untreated animals, the stabilization of the score occurred in the groups of animals treated with NMDA receptor antagonists only on day 6 (89%±2.3 and 88%±2.5, for animals treated with S-(+)-Ketamine and 7-CK, respectively). A possible explanation for this difference may be that the (partial) blocking of NMDA receptors is delaying neosynaptogenesis, where they have a neurotrophic effect, and thus retarding functional recovery.

Administration of the two NMDA antagonists had on the other hand a substantial impact on the number of false positives (FIGS. 4B and 5B). Unlike the untreated animals or those treated with D-JNKI-1, there could be no group observed, where a permanent increase in the number of false positive responses occurred after an initial transitory increase. There was either no increase in false positives at all (group 1; n=5 and n=4 for animals treated with S-(+)-Ketamine and 7-CK, respectively), where false positives of 0.22±0.22 were observed on days 0 and 1, or just the reversible increase right after the acoustic trauma (group 2; n=5 and n=6 for animals treated with ketamine and 7-CK, respectively), with the number of false positives rising from 0.2±0.2 (S-(+)-Ketamine) and 0.33±0.21 (7-CK) on day 0 to 5±0.48 (S-(+)-Ketamine) and 4.66±0.42 (7-CK) on day 1. There were thus no observations of the onset of a persistent tinnitus following the incidence of transitory tinnitus. These results demonstrate that the local administration of NMDA receptor antagonists to the cochlea suppresses persisting tinnitus induced by cochlear excitotoxicity.

The invention claimed is:

1. A method for treating tinnitus induced by cochlear excitotoxicity in a human, the method comprising administering to the human a therapeutically effective amount of a pharmaceutical composition comprising the NMDA receptor antagonist ketamine, effective to suppress or reduce NMDA receptor mediated aberrant activity of the auditory nerve in the human in need of such treatment and correlating the administration of ketamine with a reduction in tinnitus and with suppressed or reduced NMDA receptor-mediated aberrant activity of the auditory nerve.

2. The method of claim 1 wherein the cochlear excitotoxicity is provoked by an occurrence selected from the group consisting of acoustic trauma, presbycusis, ischemia, anoxia, and sudden deafness.

3. The method of claim 1 wherein the pharmaceutical composition is administered topically/locally via the round window membrane or the oval window membrane to the inner ear.

4. The method of claim 1 wherein the pharmaceutical composition is administered topically/locally to the inner ear.

5. The method of claim 2 wherein the cochlear excitotoxicity is acute.

6. The method of claim 2 wherein the cochlear excitotoxicity is repeated.

7. The method of claim 2 wherein the cochlear excitotoxicity is prolonged or chronic.

8. A method for treating tinnitus induced by cochlear excitotoxicity in a human, comprising administering to the human a therapeutically effective amount of a pharmaceutical composition comprising ketamine.

9. The method of claim 8, wherein the normal auditory neurotransmission is not affected.

10. The method of claim 8, wherein the pharmacological composition comprises a ketamine analog, a ketamine derivative or a ketamine enantiomer.

11. The method of claim 8, wherein the ketamine is (S)-ketamine.

12. The method of claim 8, wherein the ketamine is enantiomerically enriched for (S)-ketamine.

* * * * *